United States Patent [19]

Haller

[11] 4,067,334
[45] Jan. 10, 1978

[54] SELF-INJECTING HYPODERMIC SYRINGE DEVICE

[76] Inventor: J. Gilbert Haller, 20 W. Andrew St., Lancaster, Pa. 17603

[21] Appl. No.: 736,761

[22] Filed: Oct. 29, 1976

[51] Int. Cl.² ............................................. A61M 5/00
[52] U.S. Cl. ............................... 128/218 A; 128/218 F
[58] Field of Search ............ 128/218 A, 218 F, 218 R, 128/224, 236, 234, 213, 216, 215

[56] References Cited

U.S. PATENT DOCUMENTS

| 2,531,267 | 11/1950 | Harnisch | 128/218 F |
| 2,591,457 | 4/1952 | Maynes | 128/218 F |
| 2,960,087 | 11/1960 | Uytenbogaart | 128/218 F |
| 3,941,130 | 3/1976 | Tibbs | 128/218 A |

FOREIGN PATENT DOCUMENTS

| 1,101,575 | 10/1955 | France | 128/218 F |
| 1,170,312 | 1/1959 | France | 128/218 F |
| 502,239 | 11/1954 | Italy | 128/218 F |
| 1,242,060 | 8/1971 | United Kingdom | 128/218 A |

Primary Examiner—John D. Yasko
Attorney, Agent, or Firm—C. Hercus Just

[57] ABSTRACT

A hand-held instrument having a handle somewhat resembling a pistol grip depending from a horizontal frame having a slide on the forward end thereof to which a conventional hypodermic syringe is connected and including a tension spring connected to the rearward end of said slide for purposes of instantly injecting the needle of the syringe into flesh. The slide is held in its rearward, cocked position by a sear and the sear is released by means of the piston of a piston and cylinder unit, the piston being operated initially to release the sear from the syringe slide to effect injecting movement thereof. A flexible bulb is supported within the handle and a finger-engageable lever engages the bulb to force fluid against the piston to cause release of the sear and continued compression of the bulb operates a finger guided for movement against the outer end of the plunger of the syringe and forces the same in discharging direction immediately after the needle of the syringe has been injected into flesh.

13 Claims, 13 Drawing Figures

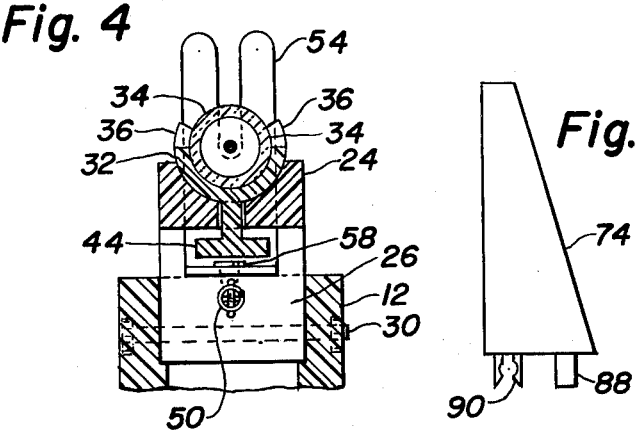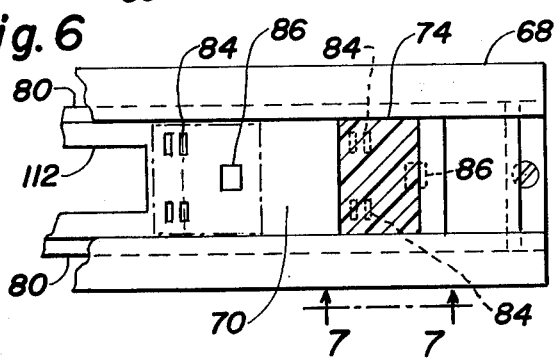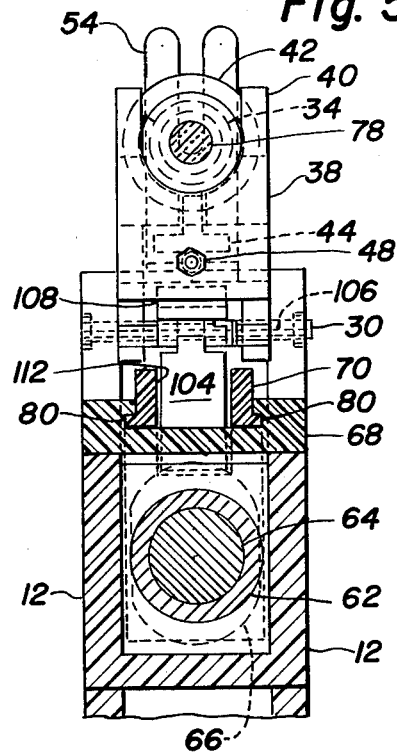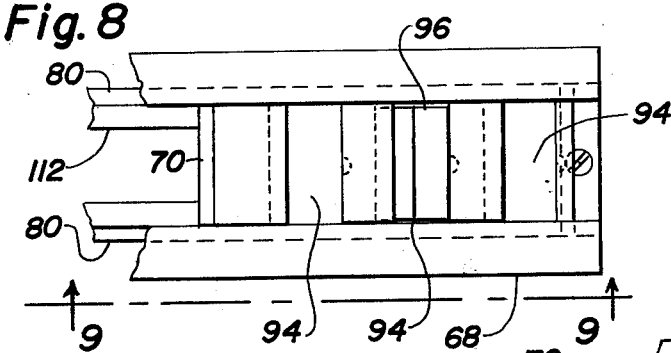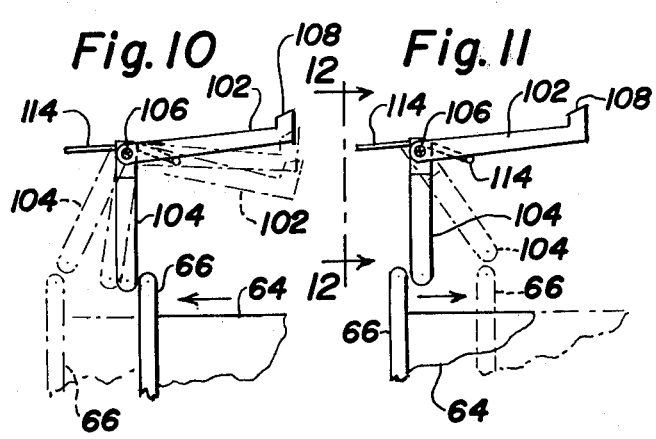

SELF-INJECTING HYPODERMIC SYRINGE DEVICE

BACKGROUND OF THE INVENTION

Millions of syringes are used daily throughout the United States relative to injecting humans as well as animals with various types of solutions and medications. Syringes for humans are also used in large quantities by victims of diabetes and a very high percentage of such victims require the injection of Insulin. It is possible for such victims to have such injections occur at home rather than in a doctor's office but many individual victims are incapable of psychologically overcoming the hesitancy of injecting themselves with a hypodermic needle.

To overcome the foregoing situation and particularly to provide syringe-injecting devices which can be operated by victims themselves to effect their own injections by themselves, a number of instruments have been developed to support needle-type syringes and by means of springs or otherwise cause an instantanous projection of the needle of the syringe into their own flesh. One example comprises U.S. Pat. No. 3,677,246, dated July 18, 1972, to Stein and also British Pat. No. 780008, dated July 31, 1957, to Palmer. In said U.S. patent, a spring effects ejection of the contents of the syringe after insertion of the needle and in said British patent, a manually operated plunger effects such projection of the contents of the syringe following insertion of the needle.

A number of developments also have provided mechanism in which a supporting frame for a syringe has a handle similar to a pistol grip and operation of trigger-like members causes movement of the plunger of the syringes to effect ejection of the contents of the syringe. Typical examples of such devices comprise U.S. Pat. No. 3,160,156, dated Dec. 8, 1964, to Tyler; U.S. Pat. No. 3,353,537, dated Nov. 21, 1967, to Knox et al.; Austrian Pat. No. 212,625, dated Dec. 27, 1960, to Hauptner; and Swiss Pat. No. 449,180, dated Nov. 8, 1966, to Sanz.

SUMMARY OF THE INVENTION

It is one of the principal objects of the present invention to provide a hand-held type of syringe injecting device which by means of a manually operated fluid cylinder and piston unit initially releases a sear to permit a spring to project the needle of a syringe into flesh, and under positive manual control, the projection of the syringe is immediately followed by pressure automatically being applied against the knob of the syringe piston to effect ejection of the contents thereof through said needle.

It is another object of the invention to employ a collapsible bulb in the handle of the device which comprises the means for projecting the body of said aforementioned piston of the cylinder and piston unit to actuate the piston of the syringe to effect such ejection of the contents thereof.

It is a further object of the invention to provide a slide mounted in guide means adjacent the forward end of the frame of the device, said slide securely supporting the barrel of a hypodermic syringe, and a second slide mounted in guide means rearwardly of said first mentioned slide is actuated by the aforementioned cylinder and piston unit to initially release said aforementioned sear and also cause an upwardly extending finger on said slide to contact the knob end of the syringe piston to cause ejection of the contents of the syringe.

Still another object of the invention is to provide a frame preferably molded from synthetic resin and having a pistol-type handle projecting from the rearward portion thereof, said handle being hollow to contain said aforementioned collapsible bulb which is depressed manually by means of a pivoted, finger-engaging lever operable through an opening in one side of said handle to engage said bulb and progressively compress it in a manner to positively eject only a desired quanity of the contents of the syringe into flesh, the same being accomplished while the syringe is in ready view of the operator.

Still another object of the invention is to provide various refinements and details which render the structure and operation of the device highly effective and fool-proof.

Details of the foregoing objects and of the invention, are set forth in the following specification and illustrated in the drawings comprising a part thereof.

BRIEF DESCRIPTION OF THE DRAWINGS

FIG. 4 is a fragmentary vertical sectional view of part of the mechanism shown in FIG. 1 as seen on the line 4—4 thereof.

FIG. 5 is another vertical sectional view of part of the device as shown in FIG. 1 as seen on the line 5—5 thereof.

FIG. 6 is a fragmentary plan view, partly in transverse section showing the detail of the mechanism shown in FIG. 1 as seen on the line 6—6 thereof.

FIG. 7 is a side elevation of a syringe-operating projecting member of the type used in the embodiment shown in FIG. 6 as viewed generally along the lines 7—7 thereof.

FIG. 8 is a fragmentary plan view similar to FIG. 6 but showing details of another embodiment of the mechanism.

FIG. 9 is a fragmentary side elevation of the mechanism shown in FIG. 8 as seen along the line 9—9 thereof.

FIG. 10 is a fragmentary side elevation of the sear mechanism and illustrating the same in full lines in its initial position and, in phantom, showing the same in released position.

FIG. 11 is a fragmentary view similar to FIG. 10 but showing in full lines the actuating piston in process of engaging the sear and, in phantom, showing the means by which the piston clears the sear in order to restore itself to initial operating position similar to that shown in full lines in FIG. 10.

FIG. 12 is a forward vertical elevation of the sear per se as shown in FIG. 11 on line 12—12 thereof.

FIG. 13 is an enlarged fragmentary vertical sectional view taken on the line 13—13 of FIG. 12.

DETAILED DESCRIPTION

Figure 1:
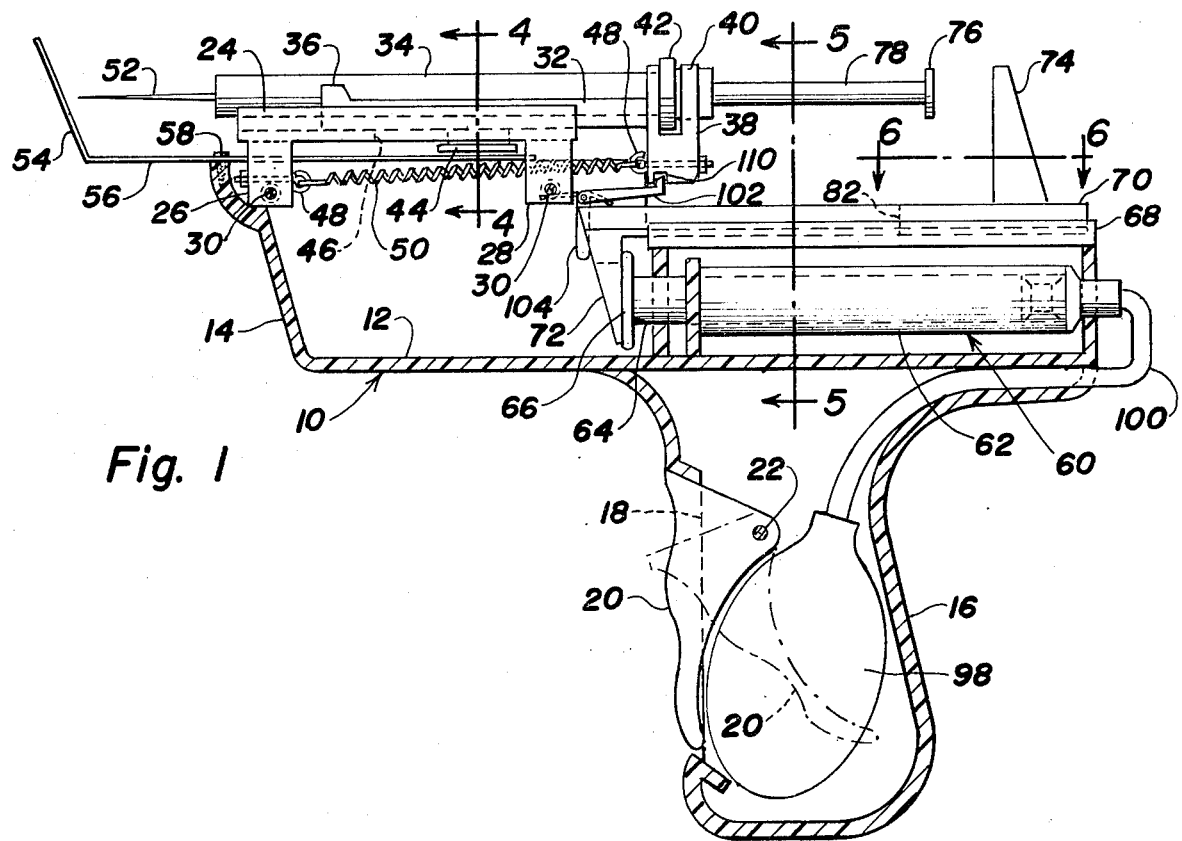
FIG. 1 is a side elevation, partly in vertical section, illustrating details of the hypodermic syringe device comprising the present invention and showing the parts thereof in initial position.
Figure 2:
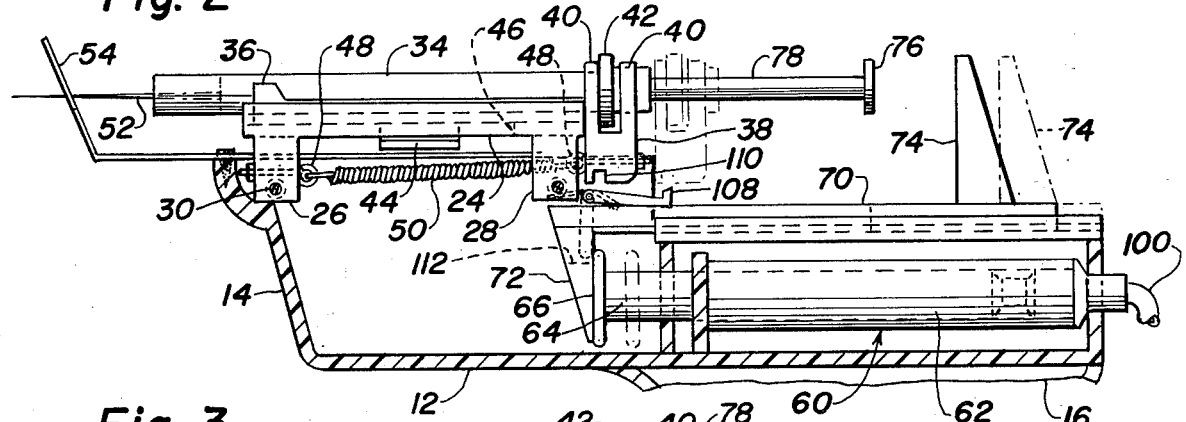
FIG. 2 is a fragmentary view similar to FIG. 2 but omitting the handle structure to decrease the size of the figure and showing the forward, injected position of the syringe following the release of the sear and constituting the initial operation of the device.
Figure 3:
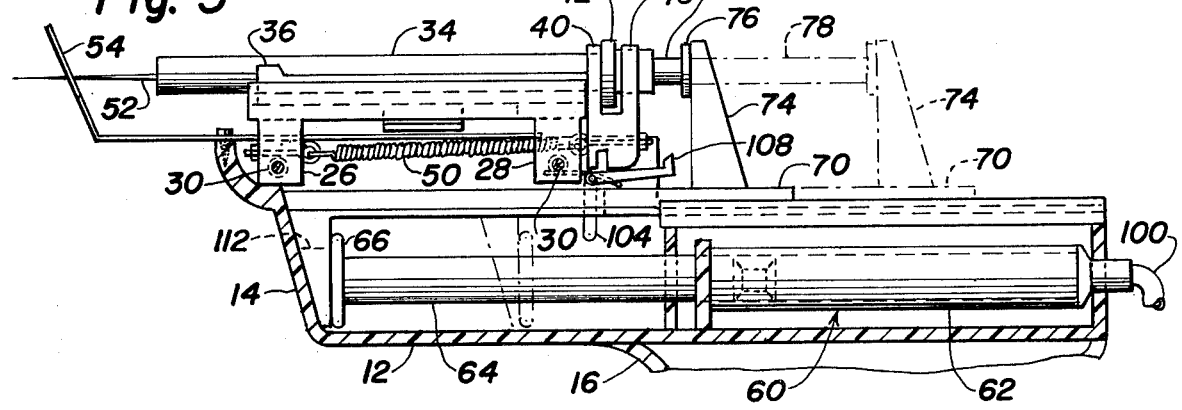
FIG. 3 is a view similar to FIG. 2 but illustrating the piston of the syringe in injected position due to being pushed by a member of the device which is motivated by a slide actuated by a piston and cylinder unit immediately above the handle.

Referring to FIGS. 1-3, it will be seen that the device comprises a unitary handle frame 10 comprising a normally horizontal frame member 12 having a forward end 14 and depending from the rearward end of the frame 12 is a handle which is molded integrally with the horizontal frame 12, said handle being hollow. The front side 18 of the handle is provided with a slot-like opening which receive a lever-type, manually operable actuator 20, an inner extention of the actuator 20 having a suitable hole therein to receive a transverse pivot pin 22 which extends between the opposite walls of the handle 16. The handle frame 10 including the horizontal frame member 12 and handle 16 readily can be molded from suitable plastic which preferably is of a rigid nature.

A first guide frame 24 has downwardly extending projections 26 and 28 with holes therein to receive transversely extending support pins 30 which extend between opposite sidewalls of the horizontal frame member 12, thereby fixedly securing the first guide frame 24 to the horizontal frame member 12. The first guide frame 24 slidably supports a syringe slide 32 comprising a channel which receives a typical hypodermic syringe 34 which has a forward pair of snap fingers 36 which secure the forward end of the syringe 34 upon the slide 32. The rearward end of said slide has a block 38 which is provided with two pairs of upstanding fingers 40 which are slotted as shown in FIG. 1 to receive oppositely extending wings 42 on the rearend of the barrel of the hypodermic syringe 34, this arrangement cooperating with the snap fingers 36 to securely but removably attach the barrel of syringe 34 to the slide 32.

Referring to FIGS. 4 and 5, it will be seen that the slide 32 has a longitudinally extending portion which, in cross section, is in the form of a tee 44, the vertical portion of which operates in a slot 46 which limits the extent of movement of the slide 32 relative to the first guide frame 24.

Projections 26 and 28 respectively have hooks or eyelets 48 to which the opposite ends of tension spring 50 are connected, said spring being operable to instantly project the slide 32 and the syringe 34 carried thereby forwardly to project the syringe needle 52 into flesh which is to receive the contents of the syringe 34. For purposes of positioning the device relative to the flesh which is to be injected, the forward end 14 of the frame member 12 has an angular shoe 54 thereon which is slotted as shown in FIGS. 4 and 5. Said shoe has a horizontal elongated extention 56 which is secured to the upper edge of the frame member 12 such as by small screws 58.

The frame member 12 also supports injecting mechanism comprising a fluid-operated unit 60 comprising a fixedly supported cylinder 62 and a piston plunger 64 having a disc-like head 66 on the forward end of said plunger; a slide guide 68 immediately above the cylinder 62; and a second slide 70 which, on the forward end thereof has a slotted, depending projection 72 which is engaged by disc-like head 66 and, on the rearward end thereof has an upstanding pusher member 74, the upper end of which is engageable with the knob end 76 of syringe plunger 78.

From FIG. 5, it will be seen that the opposite sides of the second slide 70 have outwardly extending guide ribs 80 which are received in complementary grooves in the walls of the channel comprising slide guide 68. The forward end of the second slide 70 is slotted back to the line 82 in FIG. 1 which is the inner end of said slot.

In one embodiment of the invention, the slide 70 is shown in plan view in FIG. 6. In this embodiment, it will be seen that there are a plurality of sets of openings 84 and 86 which respectively receive a locating lug 88 on pusher member 74 and pairs of snap fingers 90 shown in FIG. 7 which are received within the openings 84 in the slide 70. Any other suitable means desired may be employed to secure the base of the pusher member 74 to the slide member 70 and it will be seen that two sets of the openings 84 and 86 are provided in order that the pusher member 74 may selectively be disposed therein and thereby provide adjustability in the movement of the second slide 70 with respect to the plunger 78 of the syringe 34.

A second embodiment of the slide 70 is shown in FIGS. 8 and 9 and in which said slide is provided with a series of projections 92 which provide therebetween a series of recesses 94 which selectively receive the lower complementary end of a second embodiment of pusher member 96 and thereby adjust the effective movement of the slide 70 with respect to the plunger 78 of syringe 34.

As referred to above, the handle 16 is hollow to receive a flexible bulb 98 which is filled with a suitable fluid, preferably of a liguid nature and said bulb is connected to one end of a flexible conduit 100 and the opposite end of the conduit is connected to the rearend of cylinder 62 as clearly shown in FIGS. 1-3. Fluid is forced from the flexible bulb 90 by operation of the actuating lever 20. As the operator pivots the actuater 20 about its pivot pin 22, the member 20 can be moved to the phantom position thereof shown in FIG. 1 and in doing so very largely depresses the bulb 98 and forces fluid therefrom against the rear end of the piston plunger 64, thereby forcing the head 66 thereof forwardly to accomplish the double function of (1) releasing the sear 102 from engagement with the block 38 by means of a movement such as illustrated diagrammatically in FIG. 10, and (2) continued forward movement of the head 66 by piston plunger 64 pushes the slide 70 forwardly until the pusher members 74 or 96 engage the button 76 on the rear end of hyprodermic syringe plunger 78 and thereby effect forward movement thereof to cause ejection of the contents of the syringe 34 through the needle 52.

As referred to above, the initial movement of the slide 70 brings the head 66 of piston plunger 64 into engagement with a depending leg 104, as shown in FIG. 10 which causes the sear 102 to pivot about transverse pivot pin 106 which extends between opposite sides of the frame member 12, as shown in FIG. 5, and thereby moves the sear 102 clockwise, thus disengaging the hook-like terminal end 108 of the sear from notch 110 in the lower face of block 38. When this occurs, spring 50 immediately contracts instantaneously and projects the syringe 34 forwardly and thus drives the needle 52 into the flesh which is to receive the contents of the syringe 34.

Continued pressure upon the flexible bulb 98 projects the piston plunger 64 and head 66 thereof forwardly, during which time the articulated sear 102 and depending leg 104 are restored to the full line positions shown in FIGS. 10 and 11, while the head 66 of plunger 64 continues to move forwardly and thereby cause pusher member 74 or 96 to move the syringe plunger 78 in discharging direction within the syringe 34, as described above. During this operation, it can be visualized particularly from FIG. 1 that the movement of the slide 70 is under positive control by the operator and immediately upon stopping movement of the actuator, the forward movement of the slide 70 correspondingly is stopped, whereby ejection of accurate quanties of the contents of the syringe 34 may be effected by observing the scale normally formed upon the walls of the cylinder of the syringe 34.

After a desired quanity of the contents of the syringe 34 have been ejected through the needle 52, the device may be restored to initial condition either by manually engaging the pusher members 74 or 96 and moving the same rearwardly which forces fluid from the cylinder 62, back through the conduit 100 into the bulb 98 or, providing the inherent nature of the material from which the bulb 98 is formed is capable of effecting self restoration of the bulb 98 to its fully extended position, complete release of the actuator 20 by the operator will permit the bulb 98 to assume its normal extended position and thereby remove fluid from the cylinder 62 by suction, thus also moving the piston plunger 64 rearwardly. However, the pusher members 74 or 96 will have to be restored manually to the rearward, initial position thereof.

During the time in which the piston plunger 64 is moving the slide 70 forwardly, after the head 66 of plunger 64 has moved forwardly beyond the depending leg 104, said depending leg extends into the longitudinal slot 112. However, when it is necessary to restore the piston plunger 64 and head 66 to the initial starting position thereof such as shown in FIGS. 1 and 2, it becomes necessary to move the head 66 rearwardly of the depending leg 104 and this is accomplished by having the sear 102 and leg 104 commoningly mounted upon pivot pin 106 and employing a spring 114 which has oppositely extending legs and a loop intermediately between the same which receives the pivot pin 106. The legs of the spring 114 operate normally to maintain the sear 102 in its latching position. However, the depending leg 104 is free to move counterclockwise to the phantom position thereof for example shown in FIG. 11 and thereby permit the head 66 of piston plungers 64 to move beneath the lower extremity of the leg 104. In order that the leg 104 will move the sear 102 from engagement with the notch 110 in block 38, it will be seen from FIG. 13 that there is a hook-like extention 116 on the upper end of the leg 104, the tip of which engages the upper surface of sear 102, whereby upon clockwise movement of leg 104, depression of the sear 102 will be effected to cause it to release notch 100 in block 38.

From the foregoing, it will be seen that the present invention provides a fullproof and durable device for effecting self-injection of the contents of a hypodermic syringe into the operators own flesh by causing initial movement of the actuator 20 to effect release of the sear 102 and thereby cause instantaneous injection of the needle 52 of the syringe 34 into the flesh of the operator, another human body, or an animal body. Then, simpliy by continuing to move the actuator 20 counterclockwise as viewed in FIG. 1, the second slide 70, by means of pusher members 74 or 96, effect discharge of the contents of the syringe 34 through the needle 52. All of this occurs without serious trauma or pain to the individual who is receiving the injection, as far as the physical operation of the device is concerned. It may be that the substance within the syringe 34 may cause some trauma upon being injected into flesh and the elimination of this by the device comprising the invention is not possible.

The foregoing description illustrates preferred embodiments of the invention. However, the concepts employed may, based upon such description, be employed in other embodiments without departing from the scope of the invention. Accordingly, the following claims are intended to protect the invention broadly, as well as in the specific forms shown herein.

I claim:

1. A portable device for holding a loaded hypodermic syringe and effecting an instantaneous injection of the needle of the syringe into the flesh followed by operation of the plunger of the syringe, said device comprising in combination, a handle frame having a longitudinal guideway, a syringe slide movable along said guideway, means on said slide to support a syringe having a needle on one end and a plunger knob on the other, a spring connected between said syringe slide and handle frame, a sear engageable with said syringe slide and operable to secure the same in a retracted position in said guideway, and injecting means on said handle frame comprising relatively movable cylinder and piston elements, one of said elements being movable to a first position to release said sear and thereby cause said spring instantly to move said slide and a syringe when mounted thereon to inject the needle thereon into flesh, and continued movement of said element thereafter effecting movement of the plunger of said syringe to inject the contents of the syringe through said needle thereof.

2. The device according to claim 1 further including a second slide engageable by said one of said elements of said injecting means unit, and said second slide having a pusher member adapted to engage the knob on the end of the plunger of a syringe when supported by said syringe slide and operable to push said plunger in a direction to eject the contents of the syringe through the needle thereof.

3. The device according to claim 2 further including a container for fluid and a conduit leading therefrom to said cylinder element of said injecting means and operable to force fluid from said container into said cylinder element to operate said piston element and move the same in a direction to move said second slide as aforesaid.

4. The device according to claim 3 in which said handle frame has a hollow hand grip receiving said container for fluid and said handle frame further having a movable manually operable member thereon adapted to engage said container and operate the same to cause fluid to be discharged therefrom to move said second slide as aforesaid.

5. The device according to claim 4 in which said container for fluid is a flexible bulb operable to discharge fluid therefrom when said manually operable member is moved against said bulb to collapse it, and the inherent nature of the flexible bulb operating to enable the same to restore itself to inflated position when said manually operable member is released.

6. The device according to claim 5 in which said manually operable member comprises a finger engageable lever pivotally connected adjacent one end to said hollow hand grip and having a portion thereof movable into said hand grip through an opening along one wall thereof to engage said flexible bulb to operate the same as aforesaid.

7. The device according to claim 2 in which said cylinder element is mounted stationarily upon said handle frame and said piston element is movable in a forward direction to initially engage said sear as aforesaid and thereafter move said second slide to eject the contents of said syringe.

8. The device according to claim 7 in which said sear has a depending leg engageable by a head on said piston element to move said sear to releasing position relative to said syringe slide and thereafter said piston head moves past said depending leg, and said leg being retractible when said piston head is returned to the initial position thereof to restore said piston head and sear to initial operating position.

9. The device according to claim 1 in which said handle frame further includes a depending hand grip adjacent one end of said frame, a slide guide fixed to said handle frame adjacent the opposite forward end thereof, said slide guide slidably supporting said syringe slide for forward injecting movement of a syringe when mounted in said syringe slide, and said spring being a coiled tension spring having opposite ends respectively connected to the forward portion of said handle frame and the rearward end of said syringe slide, and means on said slide guide and syringe slide limiting the forward injecting movement of said syringe slide.

10. The device according to claim 9 in which the forward end of said spring is connected to the forward end of said slide guide, and the rearward end of said slide guide supporting said sear.

11. The device according to claim 10 in which said injecting means comprises a second slide guide mounted stationarily upon said handle frame adjacent the rearward end thereof at a level below said first mentioned slide guide and supporting another slide, and a cylinder and piston unit below said second slide guide, said cylinder being stationary and said piston being movable by fluid pressure forward initially to engage said sear to release it from said syringe slide and continued movement being operable to engage the knob of a syringe when positioned on said syringe slide to move said plunger in ejecting directon.

12. The device according to claim 11 in which said another slide has an upstanding pusher member thereon adapted to engage said knob on the outer end of the plunger of a syringe, and means adjustably positioning said pusher member linearly upon said slide.

13. The device according to claim 11 in which the rearward end of said syringe slide has upstanding support members with vertical slots therein adapted to receive conventional wings on one end of a syringe cylinder opposite the discharge end to position a syringe cylinder against longitudinal movement thereof relative to said handle frame.

* * * * *